(12) United States Patent
Emans

(10) Patent No.: US 9,029,297 B2
(45) Date of Patent: May 12, 2015

(54) ARRAY PRINTING

(71) Applicant: CSIR, Pretoria (ZA)

(72) Inventor: Neil Emans, Pretoria (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 14/076,027

(22) Filed: Nov. 8, 2013

(65) Prior Publication Data

US 2014/0066333 A1    Mar. 6, 2014

Related U.S. Application Data

(63) Continuation of application No. 14/115,859, filed as application No. PCT/IB2012/053784 on Jul. 25, 2012.

(30) Foreign Application Priority Data

Jul. 25, 2011 (ZA) .................................. 201105478

(51) Int. Cl.
*C12N 15/10* (2006.01)
*B01L 3/02* (2006.01)
*B01J 19/00* (2006.01)

(52) U.S. Cl.
CPC ........... *C12N 15/1093* (2013.01); *B01L 3/0262* (2013.01); *B01L 2300/0819* (2013.01);
(Continued)

(58) Field of Classification Search
CPC .................................................... C12N 15/1093
USPC ........................................................ 506/9, 30
See application file for complete search history.

(56) References Cited

U.S. PATENT DOCUMENTS 6,544,790 B1 *  4/2003 Sabatini ....................... 435/455
6,762,061 B1    7/2004 Borrelli et al.
(Continued)

FOREIGN PATENT DOCUMENTS

WO    WO-0170400 A1    9/2001
WO    WO-03056293 A2   7/2003
(Continued)

OTHER PUBLICATIONS

International Application Serial No. PCT/IB2012/053784, International Search Report mailed Feb. 1, 2013, 7 pgs.
(Continued)

*Primary Examiner* — Christopher M Gross
*Assistant Examiner* — Richard L Manteuffel
(74) *Attorney, Agent, or Firm* — Schwegman Lundberg & Woessner, P.A.

(57) ABSTRACT

The invention provides a method of printing, onto a substrate (12), an array (14) of spots of reagent compositions for use in a chemical and/or biochemical analysis. The method includes displacing an array of reagent composition containing capillary tubes (22) arranged alongside one another from an inoperative position to an operative position in which open ends of the capillary tubes (22) simultaneously impinge against a substrate and thereafter displacing the array of tubes (22) from the operative position back to the inoperative position. The invention extends to a printing apparatus (10), a method of printing a layered array of spots of reagent compositions, a method of introducing reagent compositions into the tubes, a reagent introducing device for introducing reagent compositions into the tubes and a printing installation which includes the printing apparatus (10) and the reagent introducing device.

27 Claims, 11 Drawing Sheets

(52) U.S. Cl.
CPC .... *B01L2300/0838* (2013.01); *B01L 2400/025* (2013.01); *B01J 19/0046* (2013.01); *B01J 2219/00369* (2013.01); *B01J 2219/00387* (2013.01); *B01J 2219/00533* (2013.01); *B01J 2219/00585* (2013.01); *B01J 2219/00612* (2013.01); *B01J 2219/00637* (2013.01); *B01J 2219/00722* (2013.01)

(56) References Cited

U.S. PATENT DOCUMENTS

| | | | |
|---|---|---|---|
| 6,951,757 | B2 | 10/2005 | Sabatini |
| 7,312,068 | B2 * | 12/2007 | Pinkel et al. ............... 435/287.2 |
| 7,413,710 | B2 | 8/2008 | Lisec et al. |
| 2001/0044157 | A1 | 11/2001 | Shaion et al. |
| 2003/0032052 | A1 | 2/2003 | Hadd et al. |
| 2003/0032198 | A1 | 2/2003 | Lugmair et al. |
| 2004/0014102 | A1 | 1/2004 | Chen et al. |
| 2007/0031410 | A1 * | 2/2007 | Harton et al. ............... 424/145.1 |
| 2007/0248971 | A1 * | 10/2007 | Maerkl et al. ..................... 435/6 |
| 2014/0066337 | A1 | 3/2014 | Emans |
| 2014/0186532 | A1 | 7/2014 | Emans |

FOREIGN PATENT DOCUMENTS

| | | |
|---|---|---|
| WO | WO-03076076 A2 | 9/2003 |
| WO | WO-2013014619 A2 | 1/2013 |

OTHER PUBLICATIONS

International Application Serial No. PCT/IB2012/053784, Written Opinion mailed Feb. 1, 2013, 8 pgs.

International Application Serial No. PCT/IB2012/053784, Written Opinion mailed Sep. 4, 2013, 8 pgs.

Cartesian Technologies, "PixSys PA Series System and Software Operating Manual", Version 2.0, (Apr. 1999), 1-53.

"International Application Serial No. PCT/IB2012/053784, International Preliminary Report on Patentability mailed Nov. 21, 2013", 9 pgs.

Bailey, Steve N., et al., "Microarrays of small molecules embedded in biodegradable polymers for use in mammalian cell-based screens", PNAS, vol. 101, No. 46, (Nov. 16, 2004), 16144-16149.

"U.S. Appl. No. 14/076,037, Non Final Office Action mailed Jun. 25, 2014", 25 pgs.

"U.S. Appl. No. 14/115,859, Non Final Office Action mailed Jun. 23, 2014", 26 pgs.

"Korean Application Serial No. 10-2014-7004707, Office Action mailed Aug. 12, 2014", 5 pgs.

Lin, S.C., et al., "Simultaneous immobilization of protein microarrays by a micro stamper with backfilling reservoir", Sensors and Actuators B, 2004, vol. 99, pp. 174-185.

"U.S. Appl. No. 14/076,037, Examiner Interview Summary mailed Jan. 29, 2015", 2 pgs.

"U.S. Appl. No. 14/076,037, Examiner Interview Summary mailed Dec. 22, 2014", 3 pgs.

"U.S. Appl. No. 14/076,037, Response filed Dec. 18, 2014 to Non Final Office Action mailed Jun. 25, 2014", 12 pgs.

"U.S. Appl. No. 14/115,859, Examiner Interview Summary mailed Dec. 18, 2014", 3 pgs.

"U.S. Appl. No. 14/115,859, Response filed Dec. 18, 2014 to Non Final Office Action mailed Jun. 23, 2014", 13 pgs.

"European Application Serial No. 12156939.6, Extended Search Report Response filed Aug. 20, 2014 to Extended Search Report mailed Feb. 11, 2014", 5 pgs.

"Korean Application Serial No. 10-2014-7004707, Response filed Dec. 12, 2014 to Office Action mailed Aug. 12, 2014", 14 pgs.

* cited by examiner

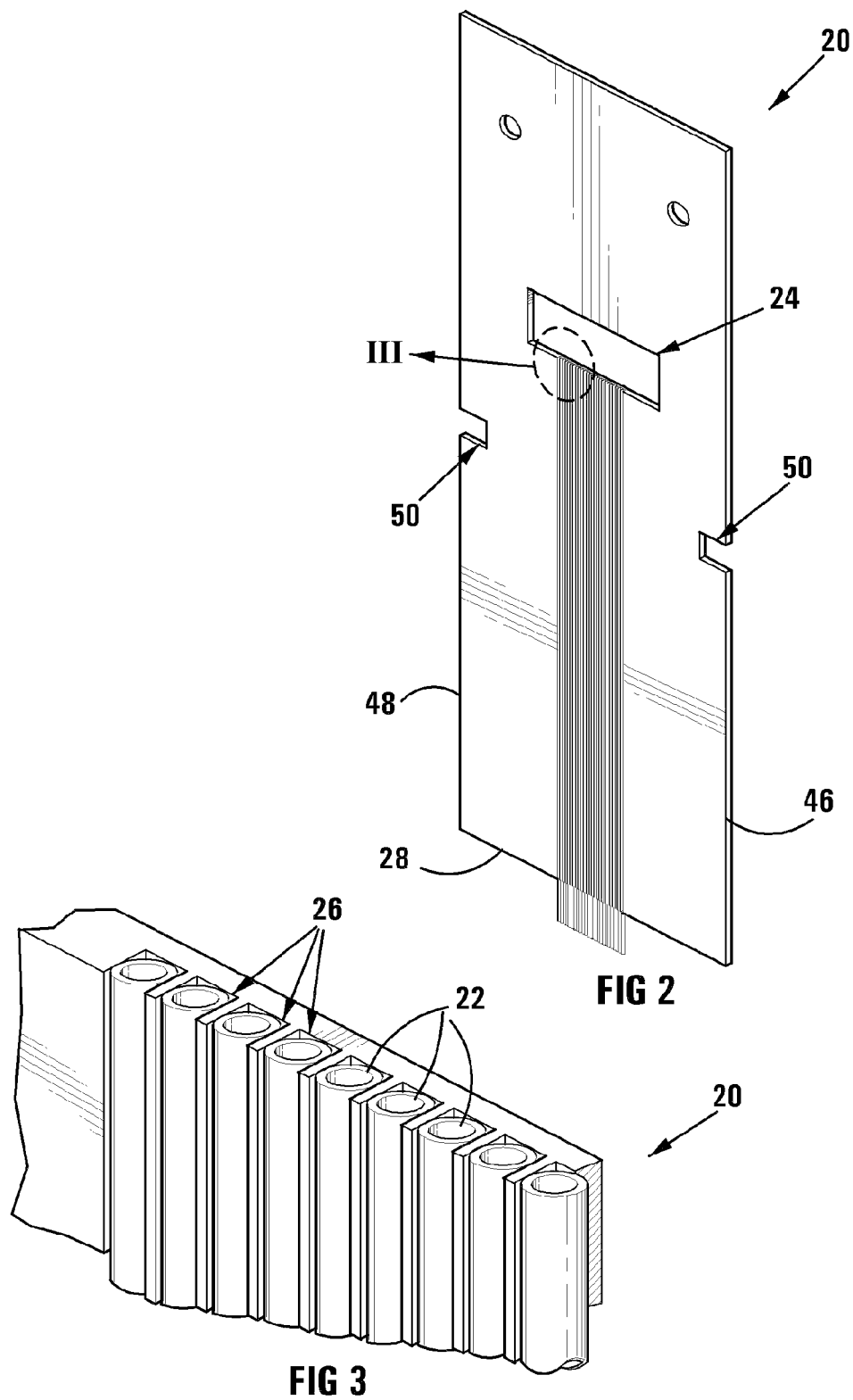

ARRAY PRINTING

CROSS REFERENCE TO RELATED APPLICATIONS

This application is a continuation of U.S. application Ser. No. 14/115,859, filed Nov. 5, 2013, which is a National Stage under 35 U.S.C. 371 of International Application No. PCT/IB2012/053784, filed Jul. 25, 2012, which claims the benefit of priority to South African Application No. 2011/05478, filed Jul. 25, 2011, all of which are incorporated herein by reference in their entirety.

THIS invention relates to array printing. In particular, the invention relates to a method of printing an array of spots of reagent compositions, a method of printing a layered array of spots of reagent compositions, a method of introducing reagent compositions into a plurality of capillary tubes, a printing apparatus for printing an array of spots of reagent compositions, a reagent introducing device for introducing reagent compositions into a plurality of parallel, open-ended capillary tubes and a printing installation which includes the printing apparatus and the reagent introducing device. As will be described more fully below, by means of the invention, a print face is provided that enables an entire array to be printed in one contact with a substrate.

The human genome comprises close to twenty thousand genes, expressed as at least a five times greater number of protein variants. Strategies for uncovering human host factors required for pathogen infection, cell division pathways address this diversity through library screening. The aim of this is similar to classical genetic mutant screens, to identify genes involved in physiology and disease through identifying desirable phenotypes. Functional genomic and genome wide screening methods for genes regulating individual events pathways have emerged with the development of expression and RNA interference (RNAi) libraries. RNAi libraries comprise a plurality of small interfering siRNAs, each a directed to silence expression of a single gene within the genome.

Given that the number of genes possibly involved in a process is potentially large, strategies for screening include systematic well-plate based screening with robotic or manual handling, requiring a significant dedicated infrastructure. Phenotypic screening by RNA interference is expensive, and is limited to research centres that possess a complex, automated, non-portable infrastructure. This has limited both the number and kind of screening that is conducted. Microtiter plate based screening is also time-consuming. In particular, the time required to conduct a microtiter plate based screen using robotics is much longer than the time to conduct a single experiment. This is because of the plurality of handling steps required to add and remove reagents, cell etc. to a large number of individual wells where each well corresponds to a discrete experiment or point in a screen. This is a particular time concern in "High Content" imaging based screens.

Instead of the use of microtitre plates, the printing of reverse transfection arrays enable many experiments to be performed within the time scale of a single experiment. In these arrays, microtiter wells are exchanged for arrayed, encapsulated siRNA/cDNA spots that are contact printed on a glass chip. These solid state arrays of encapsulated cDNAs and siRNAs are then overlaid with cells cultured on top of the arrays. In particular, each printed spot performs as a single functional genomic experiment that can be read out through automated imaging and analysis. The high density of reverse transfection arrays compared to microtiter plates results in faster screening, with many thousand experiments being performed within the time course of a single conventional experiment. Further, reverse transfection array require far fewer handling steps compared to microtiter plate based approaches because of the inherent miniaturization factor in arrays compared to microtiter plates. A typical array comprises three to four thousand individual experiments in a single vessel and is equivalent to many more microtiter plates without the need for well by well pipetting and handling. However, current reverse transfection array production technology is complex, demanding, requires expensive dedicated infrastructure, is incapable of printing an entire array in one contact and is thus limited in scale.

There is thus a need for a printing technology which adequately meets the challenges presented by the printing of such arrays, which involves the deposition of a large number of differing reagent compositions. Further, the printing of such arrays requires a printing technology that can adequately function with a composition which typically inter alia includes a transfection reagent, such as a lipid. Such compositions are relatively viscous, which can render them unsuitable for conventional printing technologies that are currently used in oligonucleotide printing, where relatively non-viscous, aqueous compositions are used.

Conventional technologies for printing arrays can be categorised into those in which there is no physical contact between the printer and the substrate and those in which there is such physical contact. Technologies in which there is no physical contact between the printer and the substrate include ink jet and bubble jet printing. A disadvantage of ink jet and bubble jet printing is that they are unsuitable for producing large arrays comprising many different reagents and cannot readily print relatively viscous compositions.

Contact printing technology, such as where metal split pins are employed which make physical contact with the substrate, also has limitations. The split pins define outwardly opening channels for receiving reagent compositions which are deposited onto the substrate when the tips of the pins make contact with the substrate. However, the channels can only receive a relatively small volume of reagent composition, typically about 100 nl, or at most about 200 nl, which means that a pin can only make contact with a substrate a limited number of times before it needs replenishment with further reagent composition. For example, the limit with siRNA printing is 10 to 15 times. Also, due to the size of the pins, the minimal spot-to-spot distance achievable by a head of pins in a single contact of the head with the substrate is about 2 to 5 mm. Further, the pins are fragile and costly. For technical and economic considerations, they need to be reused but this means that they require to be washed free of other reagents, which takes time and slows printing as well as reduces the practical efficiency of the pins. Still further, split pins are poorly suited for handling relatively viscous compositions required in reverse transfection arrays, which tend to clog the channels of the pins.

Another technique for printing microarrays is by means of photolithography, as is described in International PCT Patent Publication Number WO 9210092 and U.S. Pat. Nos. 5,405,783 and 5,770,722. These techniques are limited to the printing of oligonucleotides, and are not suitable for printing a plurality of siRNAs using relatively viscous compositions. Further, they are unsuitable for producing large arrays with many differing reagent compositions.

Further, microarrays produced using commercial microarrayers exploiting ink jet, photolithographic or contact printing elements as described above are typically used in combination with robotic movements involving a large number of iterative steps to print an array. This is because the number of printing elements is far fewer than the number of arrayed features printed on the substrate. While widely used for printing oligonucleotide or similar arrays, these methods are inefficient for producing arrays of siRNAs or of expression cDNA vectors for gene by gene functional genomic investigation owing to the large number of different reagent compositions in such arrays. In particular, the iterative nature of current printing technology reduces the production volume, flexibility and speed in the printing of such arrays. Further, the robotic equipment required for iterative steps is expensive and is unsuited for production of reverse transfection arrays on a mass scale.

Thus, current printing technology is particularly inefficient for producing functional genomic arrays. It is well known that the conventional commercial microarrayers have a maximum capacity of one genome printed on arrays each containing 384 spots every 7 hours. This only permits the production of ten genomes in about 70 hours, which imposes a limit on the utility of such devices. This invention seeks to provide for a more rapid, large scale production of arrays, and to overcome, or at least ameliorate, one or more of the limitations indicated above of existing microarrayers.

Further, there is a need for printing layered (i.e. superimposed) arrays of coincident spots. The printing of such arrays can be useful in various applications. One such application is the printing of an array of compound spots and the printing thereover of an array of a polymer spots coincident therewith. The use of such spots is disclosed in Bailey, S. N., D. M. Sabatini, and B. R. Stockwell, Microarrays of small molecules embedded in biodegradable polymers for use in mammalian cell-based screens, Proceedings of the National Academy of Sciences of the United States of America, 2004, 101 (46): p. 16144-9 and in WO03056293 (Whitehead Institute for Biomedical Research et al).

In WO03056293, a method is described for the printing of a compound spots and of polymer spots thereover and in register therewith, wherein diffusion of the compound is restricted but release of the compound into cells overlaid on to the spots is permitted, the printing of arrays of such spots being produced using the split pin printing technology. The superimposition of the arrays of coincident spots requires, however, near perfect registration of the compound spots with the polymer spots. In addition to the problems with split pin printing technology mentioned above, the use of such technology to print superimposed arrays of coincident spots is prone to error attributable to mechanical misalignment which results in the spots of the arrays not being satisfactorily in register. A method for producing superimposed arrays of coincident spots more easily, reliably, rapidly and at greater scale would therefore be highly desirable, and would facilitate more widespread use of such arrays.

According to a first aspect of the invention there is provided a method of printing, onto a substrate, an array of spots of reagent compositions for use in a chemical and/or biochemical analysis, which method includes:

displacing an array of reagent composition containing capillary tubes arranged alongside one another and each having at least one open end, with the open ends of the tubes being aligned, from an inoperative position to an operative position in which the open ends of the capillary tubes simultaneously impinge against a substrate, so that at least some reagent composition from the capillary tubes is thereby deposited on the substrate as spots, thereby to form an array of spots of the reagent compositions on the substrate; and thereafter displacing the array of capillary tubes from the operative position back to the inoperative position.

Each capillary tube thus deposits a spot of an individual reagent composition on the substrate.

The method may include, after the array of capillary tubes has been displaced back to its inoperative position, or while it is being so displaced, replacing the substrate bearing the array of spots with another substrate, and repeating the displacement of the array of capillary tubes from its inoperative position to its operative position, and back to its inoperative position.

The capillary tubes may thus extend parallel to one another. Preferably, the capillary tubes are arranged vertically, with the displacement of the capillary tubes also being vertically.

The open ends of the tubes are thus located or terminate in the same plane; this plane is preferably horizontal when the tubes are arranged vertically.

The capillary tubes may be of plastics material or, preferably, of glass. The inner diameters of the capillary tubes are typically less than 1 mm, with all the capillary tubes having the same nominal inner diameter.

The method may include, before the displacing of the array of capillary tubes from the inoperative position to the operative position, forming the array of capillary tubes by supporting the capillary tubes on or against a plurality of supporting elements, with each supporting element supporting a plurality of the tubes.

The method may include stacking the supporting elements into a print head assembly, with the displacing of the capillary tubes being effected by moving the print head assembly.

The reagent compositions may, for example, include siRNA, encapsulated siRNA, cDNA, oligonucleotides, proteins or cells. The method may for example be of use in producing a microarray of small interfering siRNAs to probe gene function through localised silencing of a plurality of individual genes ('genome wide screening').

The supporting elements may each define a plurality of grooves for receiving the tubes, one groove for each tube, and the tubes may be displaceable along the lengths of the grooves. The print head assembly may include a displacement means for simultaneously displacing the tubes.

The method may include introducing reagent compositions into the capillary tubes. The introduction of the reagent compositions into the capillary tubes of each supporting element may be by means of a plurality of troughs defined by a reagent introducing device, with the troughs being positioned adjacent and in register with the open ends of the tubes of the supporting element. The reagent introducing device may be in the form of a plate. The reagent compositions may flow out of the troughs and into the tubes by capillary action. In order to bring the open ends of the tubes into a position in which they are adjacent and in register with the troughs, the reagent introducing device may be positioned at its location by means of a locating device and the supporting element may be secured to a moveable mechanical arm and displaced by the arm to a position in which the open ends of its tubes are adjacent and in register with the troughs when the reagent introducing device is at its location. Conveniently, each trough may taper in width towards a narrowed trough portion, and the method may include introducing the reagent compositions into the troughs at or near their widest portions, with the reagent compositions flowing out of the troughs and into the capillary tubes at the narrowed portions of the troughs.

While the capillary tubes can be located vertically, they can instead be located at an angle to the vertical. It is believed that, by locating the capillary tubes at an angle while the reagent composition is introduced into them, they can be filled to a greater extent through capillary action than would be the case if they are located vertically.

According to another aspect of the invention there is provided a method of printing, onto a substrate, layered arrays of spots of reagent compositions for use in a chemical and/or biochemical analysis, which method includes:

printing a first array of spots, the printing of the first array of spots including:

displacing an array of reagent composition containing capillary tubes arranged alongside one another and each having at least one open end, with the open ends of the tubes being aligned, from an inoperative position to an operative position in which the open ends of the capillary tubes simultaneously impinge against a substrate, so that at least some reagent composition from the capillary tubes is thereby deposited on the substrate as spots, thereby to form an array of spots of the reagent compositions on the substrate; and thereafter displacing the array of capillary tubes from the operative position back to the inoperative position; and printing over the first array of spots at least one further array of spots, the printing of the further array of spots including:

displacing another array of reagent composition containing capillary tubes arranged alongside one another and each having at least one open end, with the open ends of the tubes being aligned, from an inoperative position to an operative position in which the open ends of the capillary tubes simultaneously impinge against the substrate, so that at least some reagent composition from the capillary tubes is thereby deposited on the substrate as spots, thereby to form an array of spots of the reagent compositions on the substrate; and thereafter displacing the array of capillary tubes from the operative position back to the inoperative position, the spots of the further array being coincident with the spots of the first array.

The method of printing the first array may be as described in relation to the first aspect of the invention.

The method of printing the further array may be as described in relation to the first aspect of the invention.

The size of the spots of the further array may the same as or different to that of the spots of the first array. Thus, the capillary tubes for printing the further array may have a diameter which is the same as or different to that of the capillary tubes for printing the first array. Similarly, the width of the grooves of the supporting elements for receiving the capillary tubes for printing the further array may be the same as or different to that of the grooves of the supporting elements for receiving the capillary tubes for printing the first array, with the pitch of the grooves remaining constant, thereby to provide for the coincident superimposition of the spots.

In this manner, an array of spots having a three dimensional structure can be created. In particular, the invention can permit the production of arrays of spots in which each spot has a plurality of layers. Arrays of such spots can provide a series of modular, adjustable samples since the properties of any of the layers can be selectively varied, one or more layers can be omitted and further layers can be superimposed. Furthermore, the order in which the layers are superimposed can also be selectively varied.

It will be appreciated that there are many possible applications for the printing of superimposed arrays. For example, a small molecule array can be printed and a polymer array can be printed coincidentally thereover, so that when the arrays are overlaid with a test element such as a biological sample (for example cells), the small molecules make contact with the test element at discrete, defined locations. The polymer may for example be PLGA (50 mg/mL MW12000-16,500 Poly (dl-lactide/glycide) 50:50 in methyl salicylate).

According to another aspect of the invention there is provided a method of introducing reagent compositions into a plurality of capillary tubes, which includes arranging a plurality of capillary tubes, each having at least one open end, alongside one another such that the open ends of the tubes are aligned;

simultaneously locating the open end of each tube in its own trough, towards a first end thereof; and introducing a reagent composition into each trough and allowing it to flow along the trough to the first end thereof where it enters the capillary tube.

According to a further aspect of the invention there is provided a printing apparatus for printing, onto a substrate, an array of spots of reagent compositions for use in chemical and/or biochemical analysis, which apparatus includes an array of capillary tubes arranged alongside one another and each having at least one open end, with the open ends of the tubes being aligned;

displacement means for displacing the array of capillary tubes from an inoperative position to an operative position and back to the inoperative position; and substrate holding means for holding a substrate so that, in use, when the array of capillary tubes is displaced into its operative position, the open ends of the capillary tubes can simultaneously impinge against a substrate held by the substrate holding means with at least some reagent composition from the capillary tubes being deposited on the substrate as spots, thereby to form an array of spots of the reagent compositions on the substrate.

The apparatus may include a print head assembly which holds the capillary tube array, with the displacement means being operably connected to the print head assembly so that it can displace the print head assembly.

The print head assembly may include a plurality of supporting elements which are stacked, with each supporting element supporting a plurality of the capillary tubes.

The supporting elements may each define an aperture which extends through the element and a plurality of grooves for receiving the tubes, one groove for each tube, with the grooves extending from the aperture to an end of the supporting element and with the tubes being received by the grooves in a snug fit, the tubes being longer than the lengths of the grooves and being displaceable along the lengths of the grooves. The grooves may for example be about 250-500 μm deep and about 250-500 μm wide or of whatever dimensions as may be suitable for the particular application of the invention. The apertures of the stacked supporting elements may be in register with one another, with the apparatus including a return plate for returning the tubes to their starting positions with respect to their supporting elements during each print cycle, each print cycle consisting of a displacement of the print head assembly towards the substrate holding means and a displacement of the print head assembly away from the substrate holding means, with the print head assembly being displaceable relative to the return plate and the return plate extending through the registering apertures and being fixed in position, and with, during at least a portion of each print cycle, the tubes projecting into the registering apertures and the return plate bearing against the tubes to keep the tubes stationary whilst the supporting elements are displaced away from the substrate holding means, thereby to return the tubes to their starting positions with respect to their supporting elements.

The apparatus can be used in a method of printing, onto a substrate, layered arrays of spots of reagent compositions for use in a chemical and/or biochemical analysis, the method including printing a first array of spots and printing thereover at least one further array of spots, the spots of the further array being coincident with the spots of the first array, as is described above.

As indicated above, the size of the spots of the further array may be the same size as or different to that of the spots of the first array. Thus, the capillary tubes for printing the further array may have a diameter which is the same as or different to that of the capillary tubes for printing the first array. Similarly, the width of the grooves of the supporting elements for receiving the capillary tubes for printing the further array may be the same as or different to that of the grooves of the supporting elements for receiving the capillary tubes for printing the first array, with the pitch of the grooves remaining constant, thereby to provide for the coincident superimposition of the spots.

The displacement means may include a motor which is connected to the print head assembly.

According to a further aspect of the invention there is provided a printing installation, which includes a printing apparatus as described above; and a reagent introducing device for introducing reagent compositions into the capillary tubes of the printing apparatus.

According to a still further aspect of the invention there is provided a reagent introducing device for introducing reagent compositions into a plurality of open-ended, capillary tubes, the device comprising a plurality of troughs, with each trough tapering in width towards a narrowed portion where the open end of one of the capillary tubes can be located, with reagent composition being introducible into a wider portion of the trough.

The troughs may be positioned in an arrangement which includes two outer portions and an inner portion located between the outer portions, with each trough extending across one of the outer portions of the arrangement and into the inner portion, and with troughs that are adjacent one another at the inner portion of the arrangement extending across opposite outer portions, and with the axes of troughs that are adjacent one another at each outer portion of the arrangement diverging outwardly away from one another. In particular, the narrowed portions of the troughs may be located at the inner portion of the arrangement and the widest portions of the troughs may be located at the outer extremities of the outer portions of the arrangement. It will be appreciated that the arrangement provides for an increased spacing between adjacent ends of the troughs at the outer portions to facilitate the introduction of the reagent compositions at the ends. It will further be appreciated that the arrangement enables the introduction of reagent compositions into closely packed capillary tubes while inhibiting cross-contamination of reagent compositions in adjacent tubes. Once the reagent compositions are introduced into the tubes, the tubes can then be used to produce a closely packed array of spots of the reagent compositions, as described above. The troughs may for example be about 250-500 μm wide and about 250-500 μm deep, or of whatever dimensions as may be suitable for the particular application of the invention.

The invention thus inter alia provides for a printing apparatus with a 'Gutenberg' style print face that enables an entire array to be printed in one contact with the substrate. This avoids the need for iterative print cycles during the production of an array and of the need for expensive robotic equipment.

The capillary tubes can each contain a unique reagent composition, which is advantageous as compared with conventional prior art printing techniques where printing elements (e.g. split pins) are re-used, which requires washing of the elements prior to the introduction therein of a different reagent, resulting in reagent loss during washing. Further, the present invention employs capillary tubes which are typically of glass, are relatively robust (in particular in relation to forces applied in the longitudinal direction of the tubes) and are inexpensive, and thus can be disposed of when the tubes are emptied of reagent composition. This permits the avoidance of washing and resultant inefficiency, reagent loss and costs. The invention thus enables a reduction of the time required for printing, reduced reagent loss, reduced contamination and a high degree of certainty in experimental spot identity from one array to another in the same production run.

Further, the use of stackable supporting elements, each supporting a plurality of capillary tubes, permits easy and efficient filling thereof with reagent compositions as described above, and permits the production of a dense array of spots. For arrays of siRNAs or of expression cDNA vectors for gene by gene functional genomic investigation, the invention can provide for the production of such an array being of a sufficient density for it to be printed on a substrate that is of dimensions that are convenient for use in conventional analysing equipment.

Use of capillary tubes also can increase the scale of printing because a capillary tube can contain a larger volume of reagent than a conventional printing element such as a split pin since, once the capillary tubes are loaded, the printer can print identical arrays in a production run which can comprise about 500-1000 arrays. This enables arrays to be printed more rapidly. A further advantage of the capillary tubes is that they can function adequately with relatively viscous reagent compositions such as lipid-containing compositions with siRNA or with expression cDNA vectors as described above.

The invention accordingly provides for the rapid production, at low cost, of a high density array with a large number of experiments, since all elements of the array can be printed simultaneously, and numerous identical arrays can be printed rapidly one after another. Since the arrays in a production run are produced under identical conditions, samples can be selected for testing from a production run, for example one sample array for every 50 arrays printed in a production run of 1000 arrays, and it can reasonably be assumed that the results obtained from the testing of the samples also apply to the other, untested arrays in the production run. This is an important improvement on prior art printers that are not capable of high volume production runs, possibly printing at best only 100-200 arrays in a production run, and that print in an iterative fashion, with the printing elements requiring washing and replenishment between printing steps, resulting in the arrays printed by such printers not being identical to one another.

The invention has further advantages in relation to the printing of layered arrays in particular. There are a wide variety of potential applications for the printing of layered arrays, one important application being the testing of small molecules, e.g. drugs. In relation to the printing of layered arrays, in addition to the numerous advantages mentioned above, the invention can importantly also provide for a more accurate superimposition of the arrays of coincident spots as compared to conventional arrayers because far fewer alignment steps are required.

The invention will now be described by way of illustrative, non-limiting examples, in which:

FIG. 2 is a schematic three dimensional view of one of the supporting elements of the printing apparatus of FIG. 1;

Figure 1:
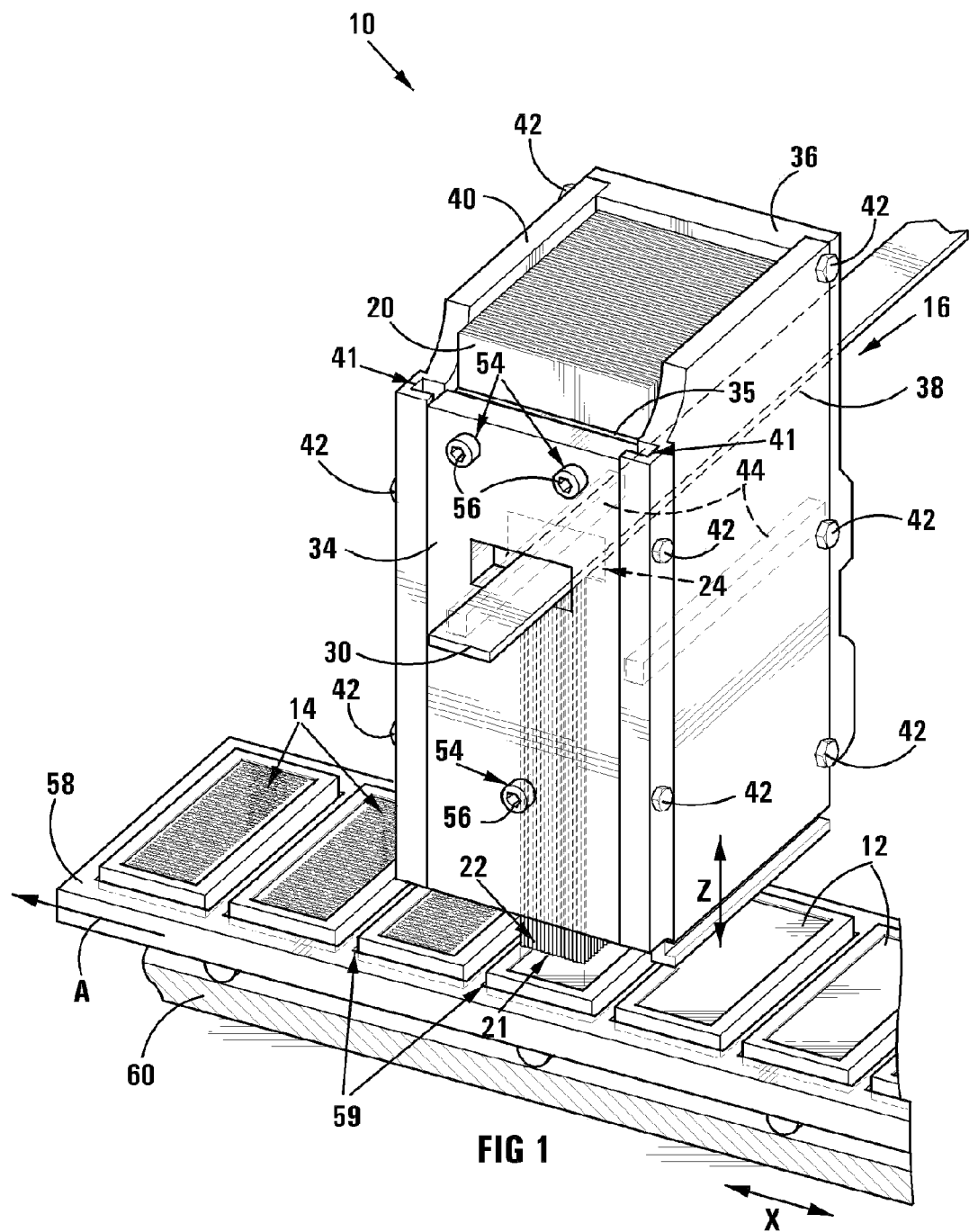
FIG. 1 is a schematic three dimensional view showing a printing apparatus in accordance with the invention.
Figure 4:
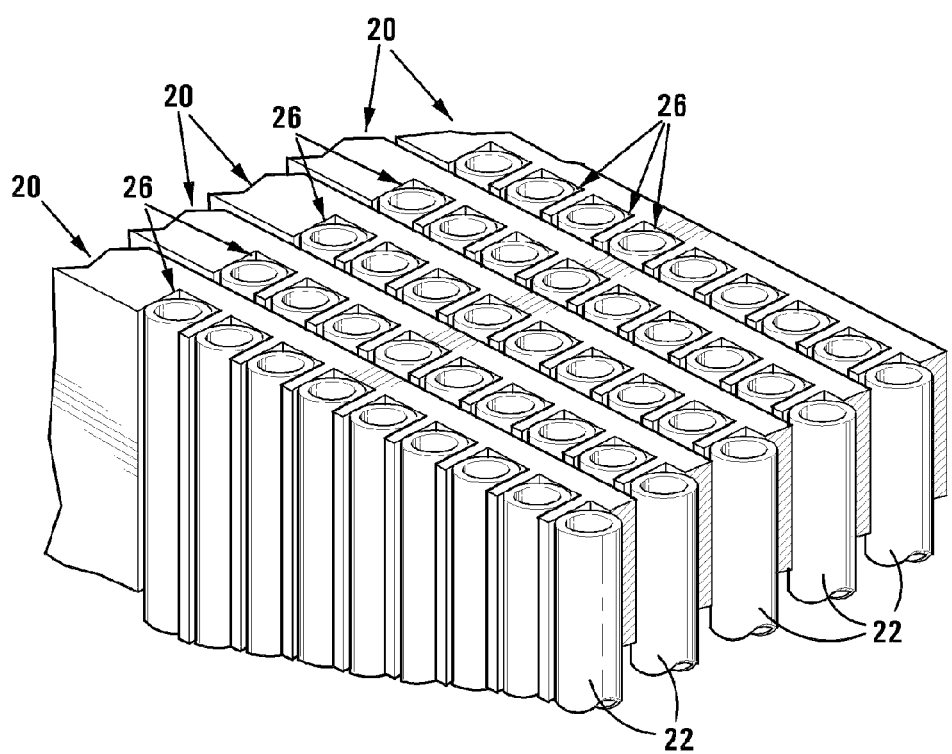
Figure 5:
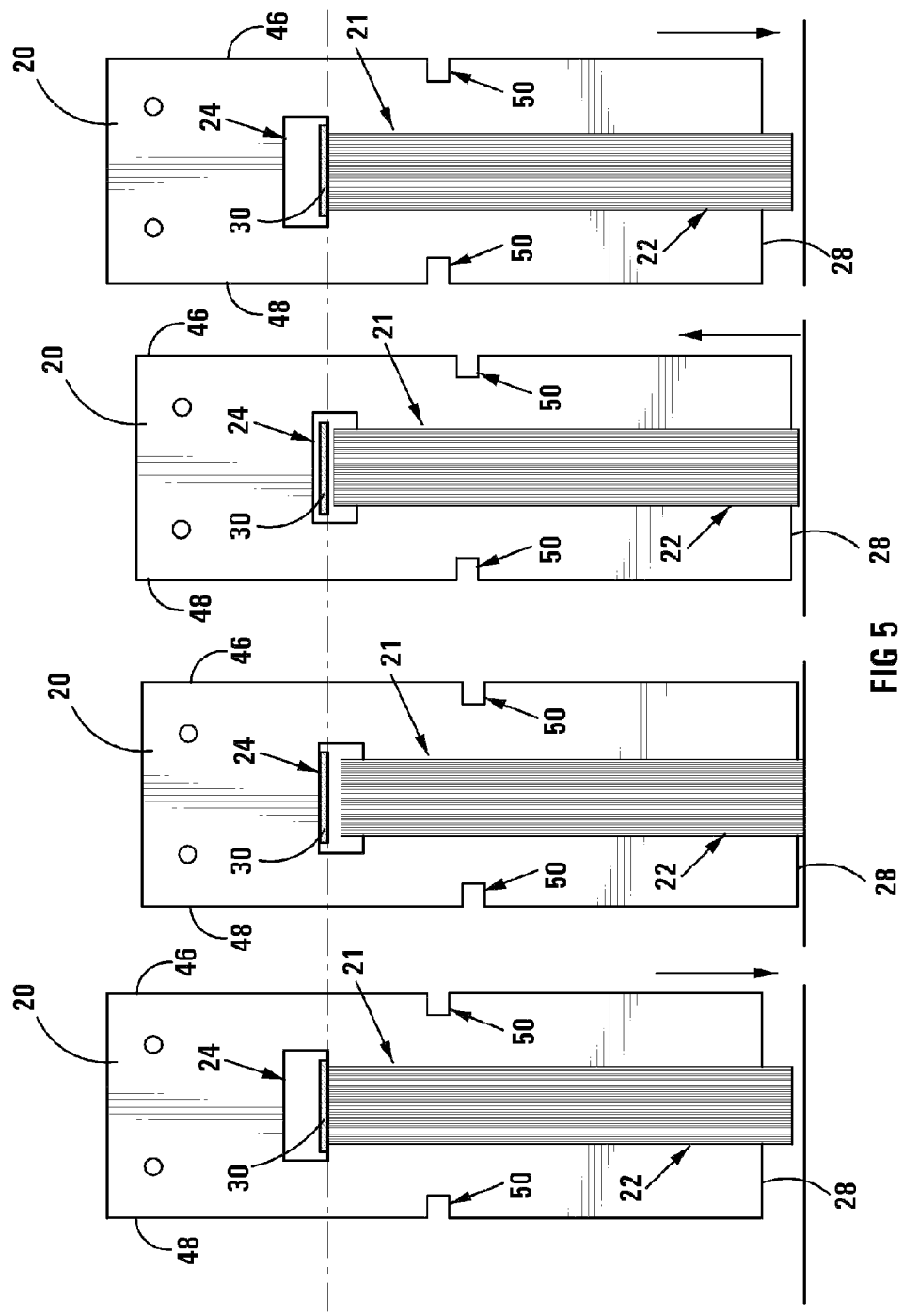
Figure 6:
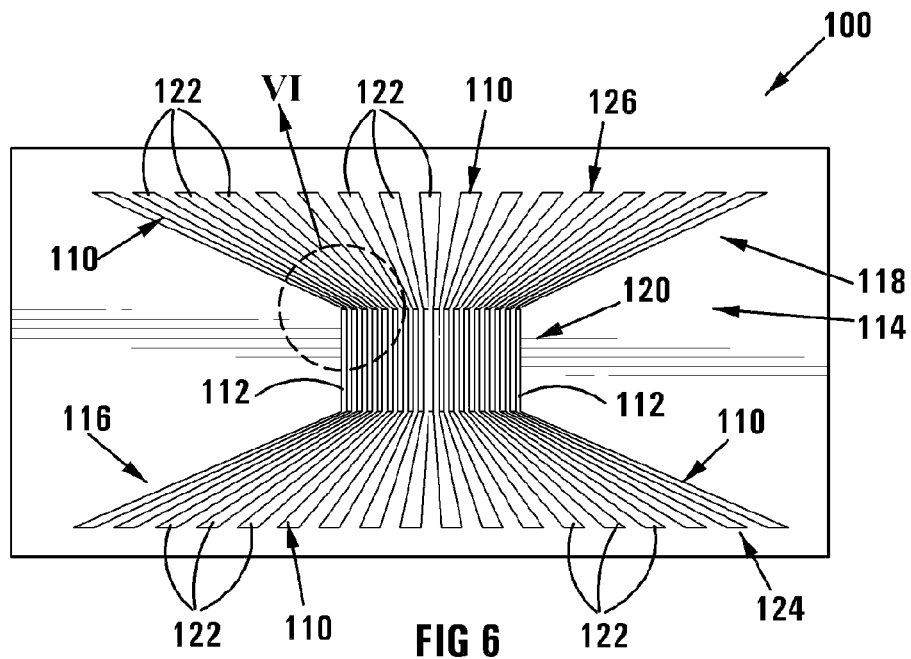
Figure 7:
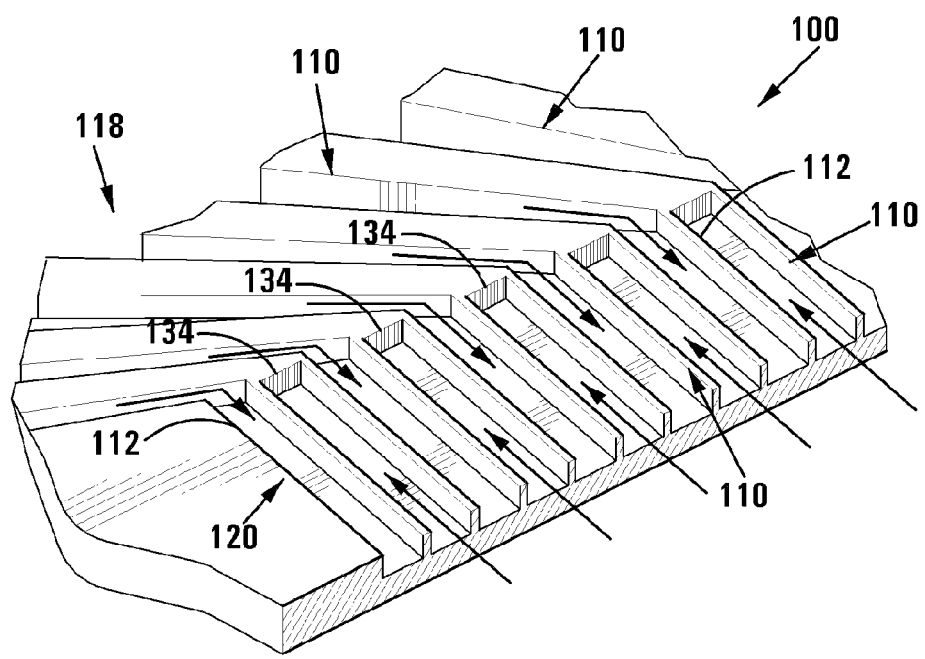
Figure 8:
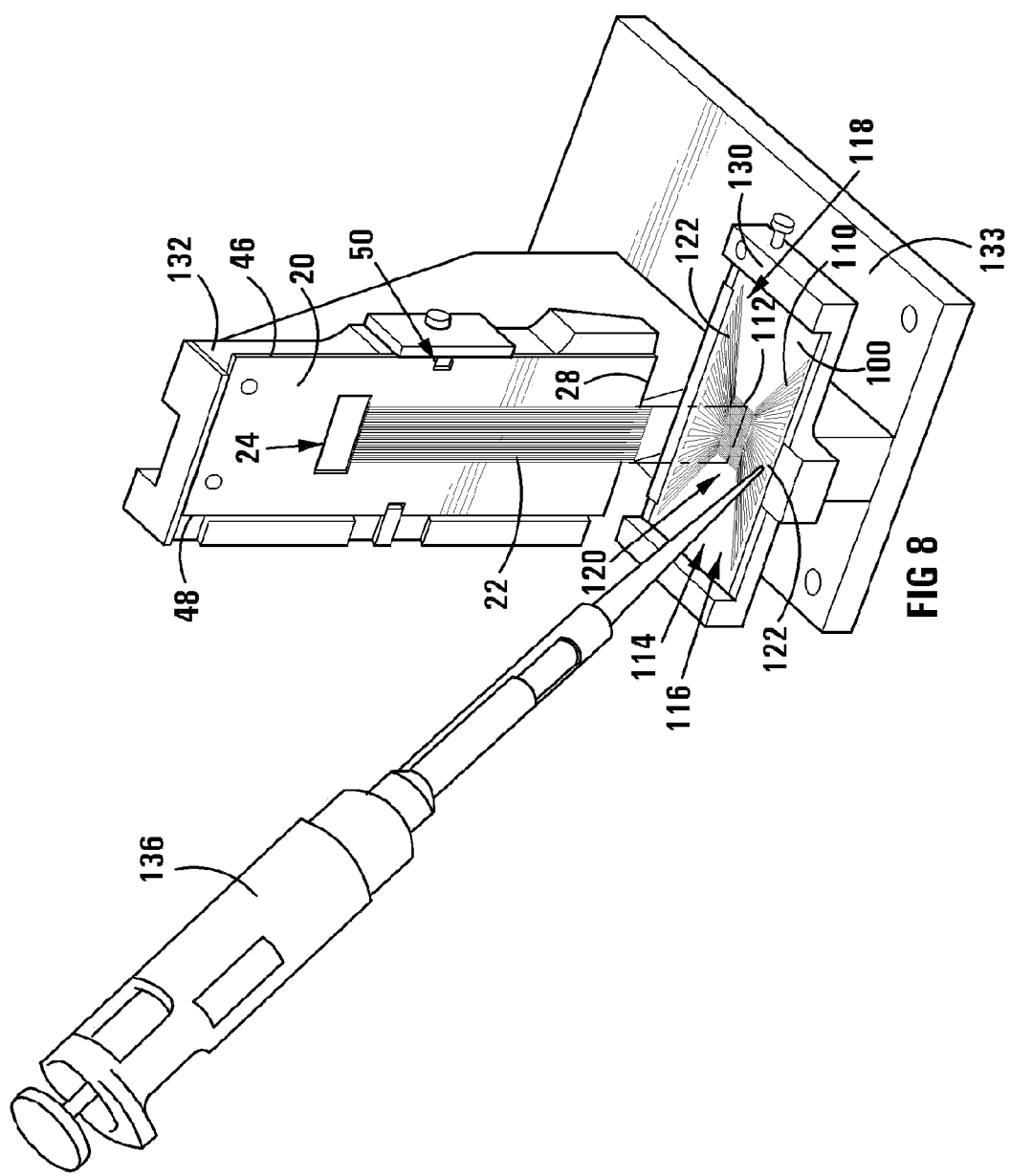
Figure 9:
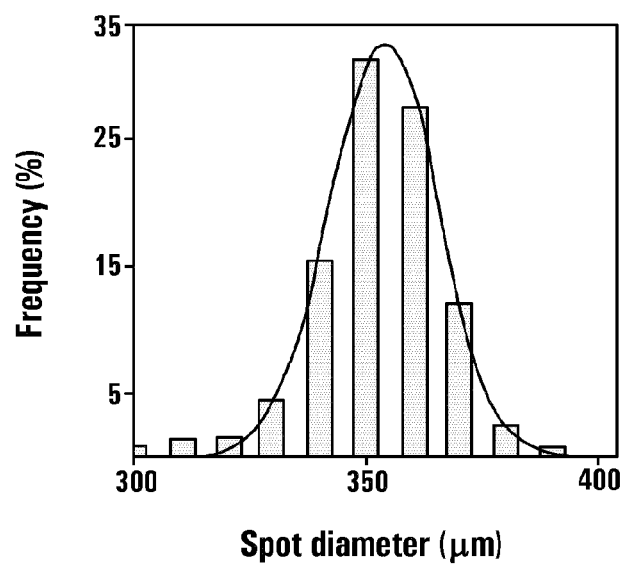
Figure 10:
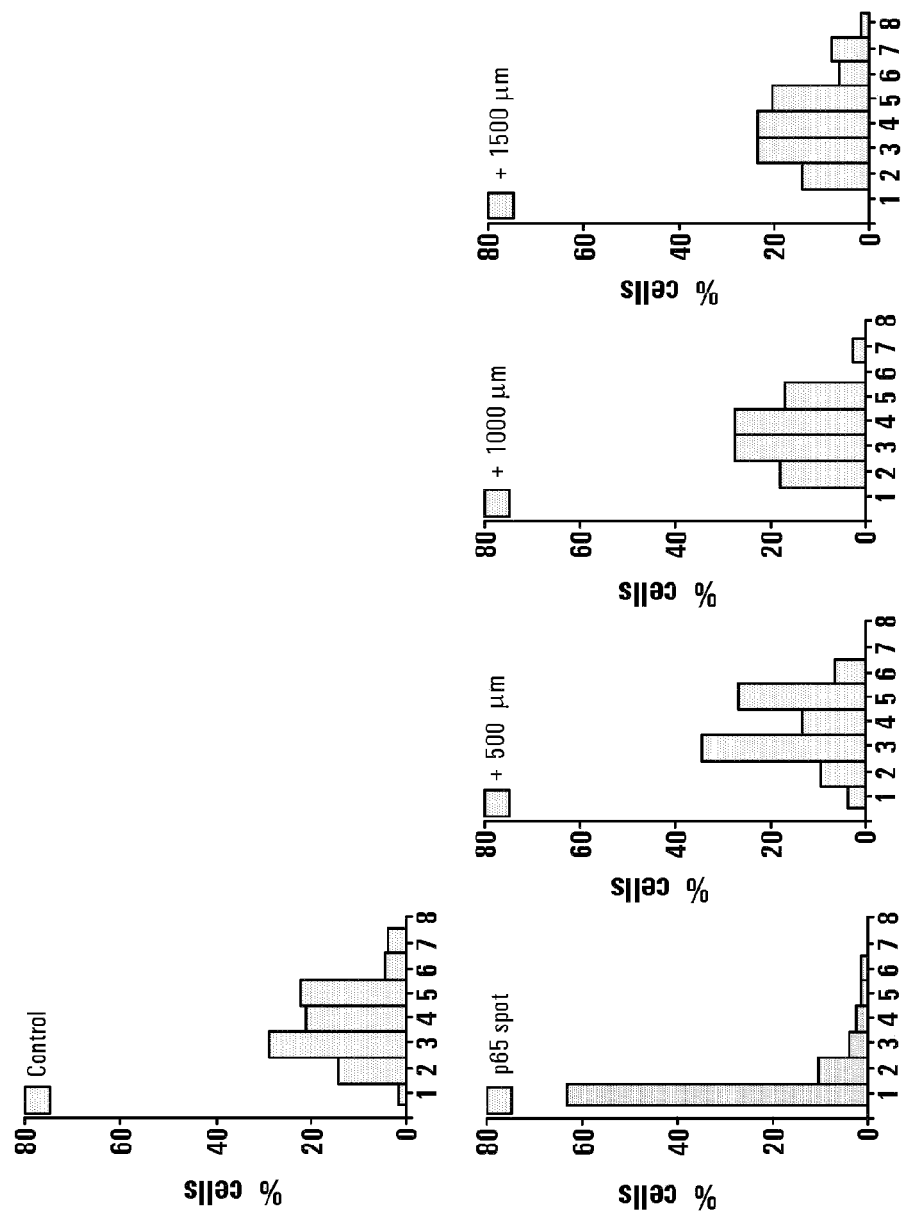
Figure 11:
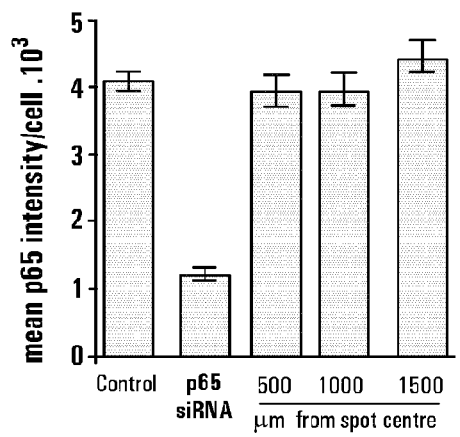
Figure 12:
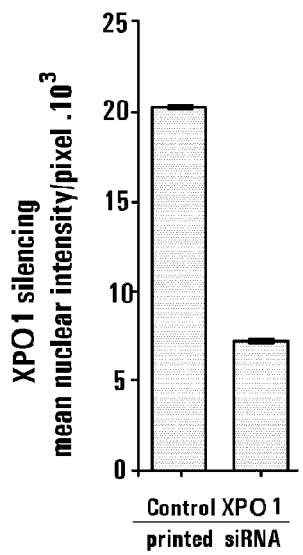
Figure 13:
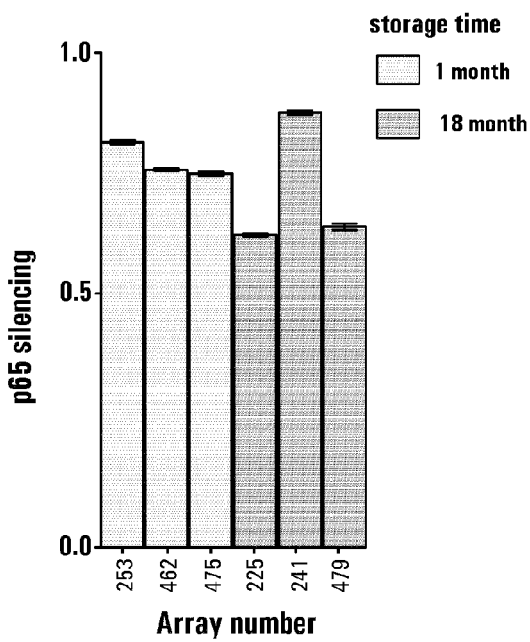
Figure 14:
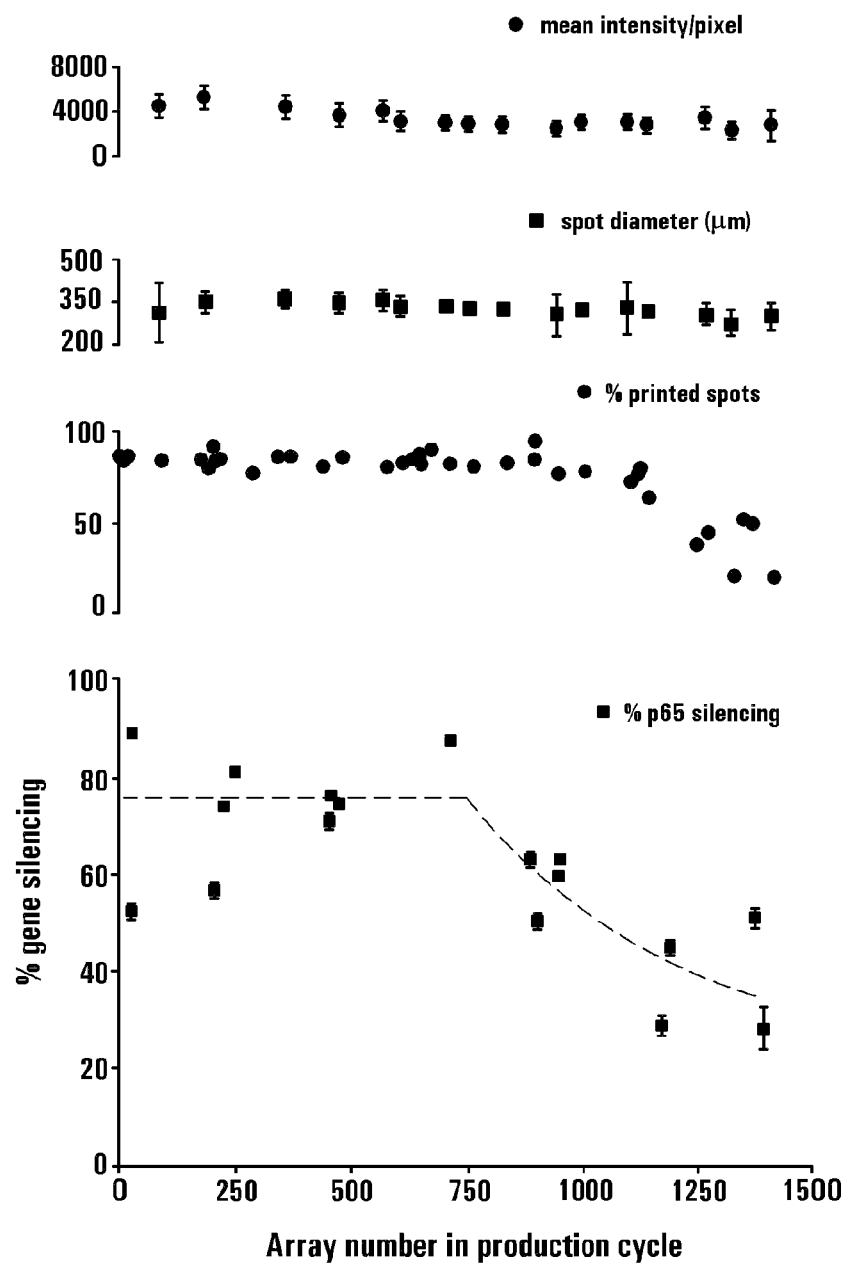
Figure 15A:
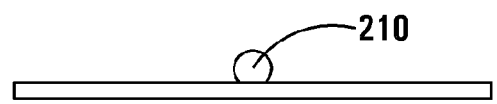
Figure 15B:
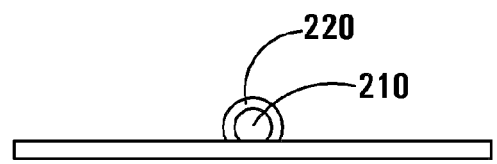
Figure 15C:
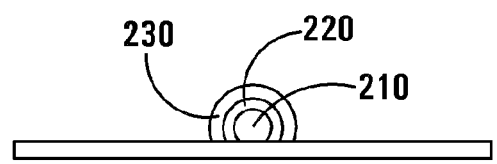

FIG. 3 schematically shows, on an enlarged scale, a detail of the supporting element of FIG. 2;

FIG. 4 schematically shows, on an enlarged scale, a portion of a stack of supporting elements of FIG. 2;

FIG. 5 schematically shows one of the supporting elements, viewed face-on, of the printing apparatus of FIG. 1, in various positions of a print cycle;

FIG. 6 is a schematic top plan view of a reagent introducing device in accordance with the invention;

FIG. 7 schematically shows, on an enlarged scale, a detail of the reagent introducing device of FIG. 6;

FIG. 8 is a schematic three dimensional view showing the introduction of a reagent composition using the reagent introducing device of FIG. 6;

FIG. 9 schematically shows the diameter distribution of the spots printed by a 330 μm outer diameter, 220 μm inner diameter borosilicate capillary tube;

FIG. 10 is a frequency distribution histogram of p65 cytoplasmic intensity per cell for a p65 siRNA spot printed with the capillary tube and for three simulated spots respectively at 500 μm, 1000 μm and 1500 μm from the p65 siRNA spot centre;

FIG. 11 shows mean p65 intensity per cell. $10^3$ respectively for a control (non-targeting) siRNA spot, p65 siRNA spot and the three simulated spots at 500 μm, 1000 μm and 1500 μm from the p65 siRNA spot centre;

FIG. 12 shows the XPO1 silencing achieved when the supporting plate of FIG. 2 holding capillary tubes was used to print a line of encapsulated XPO1 siRNA;

FIG. 13 shows a comparison of p65 silencing achieved after cells were overlaid on arrays printed by the printing apparatus of FIG. 1 at one month and at 18 months after printing the arrays;

FIG. 14 shows the variation of spot mean intensity, spot diameter, percentage of spots printed and the p65 silencing achieved over a print cycle of 1400 arrays by the printing apparatus of FIG. 1; and FIGS. 15(a) to 15(c) schematically show spots printed in accordance with the invention, successive layers being superimposed on previously printed layers.

Referring to FIGS. 1-5, a printing apparatus in accordance with the invention is generally designated by reference numeral 10. The printing apparatus 10 is for printing, onto a plurality of substrates, arrays 14 of spots of reagent compositions for use in a chemical and/or biochemical analysis. The substrates each comprise a base plate 12 which is of quartz glass with a coating of poly-1-lysine. In this example the reagent compositions include siRNAs for genome-wide screening but it will be appreciated that the invention can be applied to the production of arrays for use in chemical and/or biochemical analyses in general. The reagent compositions in this example each also include a lipid, gelatin to entrap the siRNA, sugar, a salt and a dye.

The apparatus 10 includes a print head assembly 16 and a displacement means (not shown) for vertically displacing the print head assembly 16, the displacement means including a motor (not shown) which is connected, by means of suitable transmission means (not shown), to a rear of the print head assembly 16. The print head assembly 16 includes eighty stacked supporting elements in the form of plates 20. The apparatus 10 includes an array 21 of glass capillary tubes 22 arranged vertically alongside one another for receiving reagent compositions, the tubes 22 being supported by the stacked supporting elements 20 (FIGS. 1 and 4). Each supporting element 20 supports thirty six capillary tubes 22. Each of the tubes 22 is open at each end. The capillary tubes 22 each have an outer diameter of 330 μm and an inner diameter of 220 μm and are of borosilicate glass. The lower ends of the tubes 22 are aligned, i.e. the lower ends terminate in the same horizontal plane.

The supporting elements 20 each define an aperture 24 which extends therethrough and thirty six grooves 26 (FIGS. 3 and 4) for receiving the tubes 22, one groove 26 for each tube 22, with the grooves 26 extending from the aperture 24 to an end 28 of the supporting element 20 and with the tubes 22 being received by the grooves 26 in a snug, frictional fit, the tubes 22 being somewhat longer than the lengths of the grooves 26 and being displaceable along the lengths of the grooves 26 (FIGS. 3 to 5). The apertures 24 of the stacked supporting elements 20 in the print head assembly 16 are in register with one another (FIG. 1) and the apparatus 10 includes a return plate 30 for returning the tubes 22 to their starting positions with respect to their supporting elements 20 during each print cycle, each print cycle consisting of a downward displacement towards one of the base plates 12 therebelow and an upward displacement away from the base plate 12. The print head assembly 16 is displaceable relative to the return plate 30. The return plate 30 is fixed in position and is supported at its rear end, in cantilever fashion, by a support (not shown). The return plate 30 extends through a passage formed by the registering apertures 24 of the stacked supporting elements 20 and, during at least a portion of each print cycle, the tubes 22 project into the registering apertures 24 and the return plate 30 bears against the projecting ends of the tubes 22 to return the tubes 22 to their starting positions (FIG. 5).

The print head assembly 16 includes front plates 34 and 35, a back plate 36 and opposing side plates 38, 40. The supporting elements 22 are stacked between the plates 35, 36, 38 and 40. The plate 34 is located in front of the plate 35. The plate 34 includes flanges (not shown) which extend into complementary, vertically extending grooves 41 respectively defined by the plates 38, 40. The plates 34, 36, 38 and 40 are fastened together with fasteners 42. The side plates 38, 40 include locating formations in the form of inwardly extending projections 44, and opposing sides 46, 48 of each supporting element 22 define complementary locating formations in the form of outwardly opening notches 50 (FIG. 2) within which the projections 44 are received. The plate 35 also defines complementary locating formations in the form of outwardly opening notches (not shown) within which the projections 44 are received. The plate 34 includes screw-threaded apertures 54, and adjusting screws 56 extending through the apertures 54. The ends of the screws 56 bear against the plate 35, which in turn causes the plate 35 to bear against the stack of supporting plates 20.

The apparatus 10 includes a base plate locating means for locating, during each print cycle, one of the base plates 12 at its location for the printing thereon of an array 14 as described below, the base plate locating means including a substrate holding means provided by wheeled acrylic tray 58 which defines a series of seventeen bays 59 in which the base plates 12 are received, one base plate 12 in each bay 59. The printing apparatus includes a drive (not shown) for linearly displacing the tray 58 along the x-axis. The tray 58 is supported on a 1 m² aluminium table 60. The print head assembly 16 is fixed in position along the x-axis, and above the tray 58. The print head assembly 16 is movable along the z-axis, i.e vertically, by means of the motor (not shown). Limit switches on the x- and z-axes automatically seek the respective home positions (not shown) of tray 58 and the print head assembly 16 via custom software communicating over RS232. The movements of the print head assembly 16 and the tray 58 and the synchronisation of the movements are controlled by software. The apparatus 10 is housed in a sealed hood (not shown), which includes an internal recirculating HEPA (300 m³/h) filter unit (not shown) and humidifier (not shown).

Each supporting plate 20 is 500 μm thick and is of stainless steel. The grooves 26 of each supporting plate 20 are each 94 mm long, approximately 375 μm wide and 250-300 μm deep. The centre-to-centre pitch of adjacent grooves 26 is 500 μm.

Referring to FIGS. 6-8, a reagent introducing device in accordance with the invention is designated generally by reference numeral 100. The device 100 is in the form of a stainless steel plate. The device 100 is for introducing reagent compositions into a plurality of parallel, open-ended, capillary tubes 22. The device 100 defines a plurality of troughs 110, with each trough 110 tapering in width towards a narrowed portion 112, where the lower end of one of the capillary tubes 22 can be located. The narrowed portions 112 are 400 μm in width. The troughs 110 are positioned in an arrangement 114 which includes two, outer portions 116, 118 and an inner portion 120 which is located between the outer portions 116, 118, with each trough 110 extending across one of the outer portions 116 or 118, as the case may be, and into the inner portion 120 (FIG. 7), the troughs 110 that are adjacent one another at the inner portion 120 extending across opposite outer portions 116, 118. The axes of troughs 110 that are adjacent one another at each outer portion 116, 118 diverge outwardly away from one another. The centre-to-centre pitch of the adjacent troughs 110 at the inner portion 120 is 500 μm i.e. the same as the centre-to-centre pitch of adjacent grooves 26 of the supporting elements 20. The narrowed portions 112 of the troughs 110 are located at the inner portion 120 and the widest portions 122 of the troughs 110 are located at the outer extremities 124, 126 of the outer portions 116, 118 of the arrangement 114. The arrangement 114 thus facilitates the introduction of reagent compositions into closely packed capillary tubes 22 while inhibiting cross-contamination of reagent compositions in adjacent tubes 22.

In use, the reagent compositions are introduced into the tubes 22 of each supporting element 20 via the troughs 110. As shown in FIG. 8, in order to bring the open ends of the tubes 22 into a position in which they are in register and in contact with the troughs 110, the device 100 is positioned at a location by means of a locating device or clamp 130. The locating device 130 and a mechanical arm 132 are supported on a common base 133. The tubes 22 are arranged alongside one another in the grooves 26 of one of the supporting elements 20, one tube 22 for each groove 26, such that the ends of the tubes 22 are aligned. The supporting element 20 is secured to the arm 132 and lowered by the arm 132 to a position in which the lower ends of its tubes 22 are in register and in contact with the troughs 110, the lower end of the tubes 22 being simultaneously located in their own troughs 110 towards first ends 134 thereof at the inner portion 120 of the arrangement 114 where, as indicated above, the narrowed portions 112 of the troughs 110 are located.

The reagent compositions are introduced into each trough 110 by means of a microsyringe 136 (alternatively a manually-operated or automated pipette) at or near the widest portion 122 of the trough 110, and the reagent compositions are allowed to flow along the troughs 110 in the directions of the arrows shown in FIG. 7 to the first ends 134 where, by capillary action, they enter the tubes 22 thereabove, with the reagent compositions being loaded via one side of the reagent introducing device 100 and then via the other. In this manner each tube 22 of the supporting element 20 is almost completely filled, with there being a gap between the top of the tube 22 and the top of the reagent composition in the tube 22. It takes about six seconds for the tubes 22 to be filled in this manner. It will be appreciated that, in an alternative embodiment of the invention (not shown), the tubes 22 could be filled to a greater degree if the supporting plates 20 were to be maintained at an angle to the vertical and used in a print head in which they are kept at that angle. Reagent compositions are introduced into the tubes 22 of the other supporting elements 20 in the same manner.

The supporting elements 20 are then stacked into the print head assembly 16 and the adjusting screws 56 are tightened so that their ends bear against the plate 35, which in turn causes the plate 35 to bear against the stack of supporting elements 20. The array 21 of the tubes 22 is displaced by means of the motor (not shown) from an inoperative position to an operative position in which the lower ends of the capillary tubes 22 simultaneously impinge against the base plate 12 therebelow, the contact time being about 2.5 s, so that at least some of the reagent composition in each tube 22 is thereby deposited onto the base plate 12 as a spot, thereby to form an array 14 of spots of the reagent compositions on the base plate 12. Thereafter, the array 21 of tubes 22 is moved back to its inoperative position. In particular, the motor causes the print head assembly 16 to move upwardly, and the tubes 22 also move upwardly by virtue of the frictional fit between the tubes 22 and the grooves 26. Towards the end of the upward motion of the print head assembly 16, the return plate 30 bears against the tops of the tubes 22 whilst the print head assembly 16 continues to move upwardly, the tubes 22 thereby being returned to their starting positions with respect to their supporting elements 20 (FIG. 5). After a print cycle, the tray 58 moves forward in the direction of the arrow A of FIG. 1 so that the next base plate 12 is positioned beneath the print head assembly 16, and the displacement of the array 21 of tubes 22 from its inoperative position to its operative position, and back to its inoperative position, is repeated.

In this example, the arrays 14 were kept under a stream of humidified air and 55-65% relative humidity (RH) during the print run. The trays 58 of printed arrays 14 are stored in dark (light-tight) and air-tight dessicators (not shown). The arrays 14 can be overlaid by cells for gene by gene functional genomic investigation.

It has been found that the size of the printed spots vary as a function of the inner diameter of the tubes 22, contact time and relative humidity. Typically, however, the spots can have diameters in the range of 100 μm to 500 μm, preferably 150 μm to 400 μm. Capillary tubes suitable for use in the invention have an outer diameter which is less than 4 mm, with wall thicknesses being less than 1 mm typically 0.1-0.5 mm; thus, their inner diameters can be less than 1 mm, typically 100 μm to 400 μm, preferably about 220 μm (www.vitrocom.com).

In the printing tests described below in which compositions including small interfering siRNAs (siRNAs) were printed, siRNA duplexes or pools of more than one siRNA were suspended in an encapsulation mix using a red fluorescent non-targeting siRNA as an optically addressable marker (red si-GLO, Thermo-Fisher, USA. www.thermofisher.com). This was done in the manner described in (Genovesio et al 2011 a Visual genome-wide RNAi screening to identify human host factors required for Trypanosoma cruzi infection *PLoS One* 6: e19733) and in (Genovesio A et al 2011b Automated genome-wide visual profiling of cellular proteins involved in HIV infection *Journal of biomolecular screening* 16: 945-958).

For tests using a transfection agent, Lipofectamine RNAi max (Invitrogen, USA. www.invitrogen.com) was used as the transfection agent.

For array immuno-labelling, arrays were mounted in a custom built watertight chamber, then washed in Dulbecco's phosphate buffered saline (PBS), fixed in 4% (w/v) paraformaldehyde: PBS, permeabilized with 1% TX100 (v/v) PBS, incubated with primary anti-p65 antibody (Santa Cruz Biotech, USA. www.scbt.com) in 10% (v/v) goat serum PBS for 60 min, washed 5×PBS; incubated with secondary antibody (Molecular Probes Invitrogen, OR, www.invitrogen.com) for 30 min, then washed 5×PBS. Nuclei were stained with 1 μM Draq5::PBS (Biostatus, Shepshed, UK. www.biostatus.com).

Cell lines were cultivated on arrays for 12 to 72 hours for quantifying reverse transfection. For screening, cells 1.5 million cells were seeded per array (24×60 mm) and cultivated in Opti-MEM (Invitrogen, USA. www.invitrogen.com) supplemented with 5% foetal calf serum (Gibco, USA) and 1% penicillin streptomycin (Invitrogen, USA. www.invitrogen.com) for 48 hours.

For analysis of the printed arrays, arrays were mounted in a water tight custom microtiter plate frame for imaging. Arrays were acquired with a point scanning confocal reader (Image express Ultra, Molecular Devices, USA. www.moleculardevices.com). 16 bit TIFF files were written directly to an external database hosted on an external 8TB server. Adaptive grid fitting was applied to identify siRNA spots in an entire array and to fit and annotate the spots. Fitted spots were exported as cropped, annotated 48 bit RGB TIFF spot images (Media Cybernetics, USA. www.mediacy.com). Analysis of spots and p65 expression levels in cells used commercial and in house algorithms. Analysis data was exported and analyzed using graphpad Prism (Graphpad prism, Graphpad USA. www.graphpad.com) and Unscrambler (CAMO software, Norway. www.camo.com).

All fine chemicals were obtained from Sigma-Aldrich (USA. www.sigmaaldrich.com). DRAQ5 was obtained from BioStatus (Shepshed, UK. www.biostatus.com). All siRNA duplexes were obtained from Thermo-fisher (USA. www.thermofisher.com). Primary antibodies were obtained from Santa Cruz Biotechnology (CA), and fluorescent secondary antibodies and all tissue culture reagents were from Invitrogen (USA. www.invitrogen.com). Transfection reagents were obtained from commercial sources. All trays and glass were sterilized with gamma irradiation before use (18K Gy: Isotron, RSA. www.isotron.com).

First, to test the feasibility of using a capillary tube for printing, a 330 μm outer diameter, 220 μm inner diameter borosilicate capillary tube was filled with a red fluorescent siRNA solution and encased in a thin stainless steel slab (not shown).

The contents of the encased capillary tube was repetitively contact printed on a glass base plate, which was imaged using a fluorescent microscope. It was found that printed spots were regular, circular siRNA spots with diameter of 351 μm±0.5 μm (SEM; n=2377) and a tight diameter distribution. In this regard FIG. 9 shows the diameter distribution of the printed spots. It was found that the size of the printed spot varies as a function of capillary tube outer diameter, contact time and relative humidity (not shown) but its diameter was in any event close to the outer diameter of the capillary tube. As in conventional array printing, the capillary tube deposited a nanoliter volume of encapsulated siRNA but, unlike with split-pin technology, the spot diameter appeared to be constrained to the capillary tube's outer diameter, and the tube continued to print for more than 1000 print cycles.

To determine the potential of spots printed by the capillary tubes for use in RNA interference experiments, siRNA directed against p65 and control (non-targeting) siRNA were respectively encapsulated with transfectant, introduced into a 330 μm outer diameter, 220 μm inner diameter capillary tube and printed on glass base plates.

The base plates were dried and overlaid with growing HeLa cells for 48 hours to allow siRNA uptake into the cells and for gene silencing to occur. p65 expression was detected via immuno-fluorescent staining of arrays and automated confocal imaging. Gene silencing was quantified following automated spot detection, then a comparison was done between p65 expression in cells transfected with control, non-targeting siRNA and in cells transfected with p65 siRNA. It was found that p65 was robustly silenced on p65 siRNA spots 48 hours after transfection, expression decreasing by more than 75% compared to cells on spotted control siRNA ($p<0.0001$, $n=5\times10^4$ cells/100 spots). Cell morphology was unaltered on spotted control siRNA regions compared to unspotted regions of the array and there was essentially no spreading of gene silencing at 500 μm from the spot centre, indicating local and constrained siRNA delivery.

More particularly, referring to FIGS. 10 and 11, gene silencing was measured using a p65 siRNA spot and three equivalent areas respectively at 500 μm, 1000 μm and 1500 μm from the p65 siRNA spot centre. FIG. 10 is a frequency distribution histogram of p65 cytoplasmic intensity per cell for the p65 siRNA spot and for the three simulated spots respectively at 500 μm, 1000 μm and 1500 μm from the p65 siRNA spot centre. As can be seen, p65 siRNA and control siRNA populations are well separated. At 500 μm, 1000 μm and 1500 μm from the p65 siRNA spot centre, the number of cells having a silencing phenotype in the areas simulating spots was the same as cells from arrays never exposed to p65 siRNA. FIG. 11 shows p65 intensity respectively for a control (non-targeting) siRNA spot, a p65 siRNA spot and the three simulated spots at 500 μm, 1000 μm and 1500 μm from the p65 siRNA spot centre. p65 silencing was quantified, and it was found that, compared to control, there was a more than 70% reduction in p65 expression within the p65 siRNA spot. Cells from the simulated spots at distances of 500 μm, 1000 μm and 1500 μm from the p65 siRNA spot centre were found to be statistically indistinguishable from the control cells ($p=0.5564$ (+500 μm). $p=0.5926$ (+1000 μm), $p=0.2268$ (+1500 μm)).

In another test, in order to determine whether there was overlap between adjacent printed spots when printed with capillary tubes 22 supported by one of the supporting plates 20 as described above, alternating troughs 110 of a reagent introducing device 100 were filled with either green or red fluorescent-labelled encapsulated siRNA. Capillary tubes 22 of one of the supporting plates 20 were filled from the troughs 110 by capillary action and the fluorescent-labelled encapsulated siRNA was printed on a glass base plate 12. It was found that there was no overlap from one filler channel to another that was detectable by imaging analysis.

To demonstrate that a row of capillary tubes 22 embedded in a printing plate produced gene silencing comparable to the silencing produced by a single capillary tube, a supporting plate 20 supporting capillary tubes 22 was used to print a line of encapsulated exportin 1 (XPO1) siRNA. FIG. 12 shows the XPO1 silencing achieved, demonstrating that a gene silencing was also achieved with a row of capillary tubes 22 supported by a supporting plate 20. The XPO1 silencing was quantified after automatic nuclear detection and image analysis using a nuclear recognition algorithm (P value<0.0001; n=2918 spots (control); 297 spots (XPO1)).

To investigate the large scale production of printing high density, two dimensional arrays using the printing apparatus 10, eighty two supporting plates 20 that are loaded with capillary tubes 22 filled with either encapsulated p65 siRNA or non-targeting control siRNA were stacked into the print head of the printing apparatus 10. The print head was thus able to print arrays each containing 36 rows×82 columns siRNA spots, thus providing 36×82 individual experiments that were identical but for the siRNA sequence. The printed array comprised alternating columns of spots of p65 siRNA and control siRNA. More than 1400 arrays were printed in less than 2 hours, and were then stored and dessicated.

The shelf life of the arrays was assessed by comparing gene silencing after cells were overlaid on arrays at one month after printing and at eighteen months after printing. As shown in FIG. 13, there was no significant decrease in array quality or silencing performance after eighteen months, indicating that stored arrays have a shelf life of at least 18 months.

Various measurements were made to determine print quality over a production cycle of more than 1400 arrays. As shown in FIG. 14, spot number, spot diameter and spot intensity showed little or no drift until about array 1000, when the capillary tubes 22 began to stop printing as their contents became exhausted, thus decreasing the number of printed spots. Less than 10% of the capillary tubes 22 never filled. It is believed that this is attributable to such tubes having broken or split tube ends caused during the manufacture of the tubes.

Arrays were sampled over the entire production cycle, and the sampled arrays were overlaid with HeLa cells and then stained, imaged and fitted to extract individual annotated spot images. Silencing of p65 expression was measured using spot detection and image extraction from fitted array images. The results of the measurements are shown in FIG. 14. For each spot, p65 expression levels were quantified in cells using nuclear detection and cell based recognition, generally for more than 2600 extracted spots per array. This corresponds to 1300 spot images for each of p65 siRNA and control siRNA cohorts, with there being approximately 55 cells (median+/− 16, n=2788) per spot. Thirty arrays were sampled across three production cycles, resulting, for each cycle, in 83,340 analyzed spots containing approximately $4.6 \times 10^6$ cell analyses and a total of more than $15 \times 10^6$ silencing analyses. It was found that ensemble gene silencing fell past array 1000 in each cycle, thus closely following the decrease in printed spots over the cycle. It was found that all capillary tubes 22 that were filled (i.e. more than 90% of the capillary tubes printed spots during the print cycle. It was also found that more than 85% of the capillary tubes 22 continued to print to the end of the cycle, with the remainder showing a gradual decrease in printing. Some capillary tubes continued printing spots to the last array, and there was robust gene silencing at the printed spots of the last array, demonstrating that there was no degradation of silencing during the print cycle. Since arrays are optically addressable through the inclusion of a red fluorescent tracer siRNA, coverage of all printed spots was ensured by imaging the arrays prior to culture. Based on the gene silencing data, it was found that the printing apparatus 10 was capable of printing 800-1200 arrays while maintaining more than 90% of the spots printed in the first contact.

As indicated above, the applicant has found that, by means of the apparatus 10, as illustrated and described above, a large number of arrays 14 can be printed before the tubes 22 are empty, which keeps reagent loss low. The apparatus 10 permits the production, in one print cycle, of very high density arrays 14, with each array 14 comprising about 2952 experiments. The applicant has found that 1000 such arrays 14 can be produced in 1-2 hours. This will, for example, advantageously enable the production of 1000 printed genomes in 70 hours.

To demonstrate the feasibility of using the printing apparatus in accordance with the invention to print layers of superimposed spots using differently sized capillary tubes for each layer, a first capillary tube of 330 μm outer, 220 μm inner diameter borosilicate glass capillary tube encased in a thin stainless steel slab was used to print a line of spots as a first layer on a glass substrate, the capillary tube being filled with a solution containing siRNA and red fluorescent dye. The spots were then imaged using a fluorescent microscope.

The spots were then dried and a second round of selected samples, also containing a red fluorescent dye, was then printed as a second layer of spots over the spots of the first layer, the spots of the second layer being co-incident with the spots of the first layer. A third layer of spots also containing a red fluorescent dye, was printed over the second layer, the spots of the third layer being coincident with the spots of the first and second layers.

Imaging with a microscope showed that the three layers of spots were successfully printed over each other, with the spots of the respective layers being co-incident with one another.

To assess the use of superimposed spots, printed in accordance with the invention, in the silencing of gene expression using siRNA, multilayered spots were produced using a "layer cake method" as now described below.

A first array spots of siRNA from stock solution was printed using 330 μm outer diameter capillaries (one of the spots being shown in FIG. 15(a) and designated by reference numeral 210). The siRNA included both red fluorescent siRNA and siRNA directed toward the NFkB subunit p65. The samples printed on the glass substrate were dried for 48-72 hours.

A second array of spots of transfection reagent (RNAi max invitrogen) was then printed coincidentally with the spots of the first array using 400 μm outer diameter capillary tubes (the second array of spots thus forming a layer 220 over the spots 210 as is shown in FIG. 15(b)). The spots were then dried for 72-96 hours.

A third array of spots of a gelatin and sucrose solution was printed coincidentally with the spots of the first and second arrays (the third array of spots thus forming a layer 230 as is showing in FIG. 15©). The spots were then dried for 3-5 days.

The printed spots were then overlaid with human cells and placed into culture for 48 hours. Controls comprising only the layers 210, 220 were also included. After 48 hours, the cells were chemically fixed and stained with antibodies directed toward p65, and then imaged.

It was found that the layer cake method described above gave comparable gene silencing to that achieved by a homogenous mixture of the same reagents only when all three layers 210, 220, 230 were printed. In particular, it was found that when only two layers 210, 220 were printed there was substantially less transfection and gene silencing, and that such silencing as was achieved by the two layers 210, 220 was not localised. Finally, it was found that there was no gene silencing when only layer 210 was printed.

p65 expression was quantified with automated cell recognition, and it was found that when all three layers 210, 220, 230 were printed, p65 expression decreased at the locations of the spots by more than 75% compared to cells on control areas of the array ($p<0.0001$). It was also found that cell morphology was unaltered on spotted control areas compared to unspotted regions of the array. The spotted control areas had 150-210 cells per spot.

To demonstrate the further utility of the geometry of "layer cake" spots, a test was performed wherein the order of the layers were varied. In this case, siRNA spots were printed so that the spots were superimposed on two layers of either spots of gelatin with spots of transfection agent superimposed thereon or spots of transfection agent with spots of gelatin superimposed thereon. In both cases, it was found that there was little or no gene silencing, and that, because the siRNAs dissolved into the cell culture medium, the spots could only be localised by physical means.

In a further test, the effect of varying the concentration of gelatin was investigated. In particular, a plurality of glass slides were printed with arrays of superimposed coincident spots to thus form spots having three layers, the first two layers of the spots respectively containing siRNA and a transfection agent, with the third layer being of gelatin, thereby to provide "layer cake" transfection arrays. The layer of gelatin capped the first two layers, the gelatin spots being larger than the spots of siRNA and of transfection agent. The concentration of gelatin was varied from 0.4% w/v to 3.2% w/v, with the reagents of the other layers remaining the same. It was found that gene silencing was more localised with increasing gelatin concentration, taking into account the known batch-to-batch variation in transfection reagent and gelatin quality. It will be appreciated that, in a similar manner, the layer cake transfection array could in principle be optimised with respect to a range of variables.

What is claimed is:

1. A method of printing, onto a substrate, layered arrays of spots, which method includes:
    forming an array of capillary tubes in or against a stackable supporting element, each capillary tube having at least one open end;
    stacking a plurality of the stackable supporting elements side-by-side into a print head assembly, with each supporting element supporting an array of capillary tubes
    using the array of capillary tubes to print a first array of spots onto the substrate;
    allowing the first array of spots to dry;
    printing, over the first array of spots, a second array of spots, the spots of the second array being at least partially coincident with the spots of the first array;
    allowing the second array of spots to dry;
    printing, over the second array of spots, a third array of spots, the spots of the third array being at least partially coincident with the spots of the second array; and
    allowing the third array of spots to dry.

2. The method of claim 1, further comprising including a nucleic acid solution in one of the arrays of spots.

3. The method of claim 1, further comprising including a transfection reagent in one of the arrays of spots.

4. The method of claim 1, further comprising including a gelatin solution in one of the arrays of spots.

5. The method of claim 1, wherein the first array of spots includes a nucleic acid solution, the second array of spots includes a transfection agent, and the third array of spots includes a gelatin and sucrose solution.

6. The method of claim 1, further comprising overlaying cells over at least one of the arrays of spots.

7. The method of claim 1, further comprising overlaying mammalian cells over the third array of spots.

8. The method of claim 6, further comprising placing the cells and at least one array of spots into culture for at least 48 hours.

9. The method of claim 6, further comprising chemically fixing and staining the cells with antibodies, and imaging the cells.

10. The method of claim 6, wherein 150 to 210 cells are overlaid per spot.

11. The method of claim 1, further comprising allowing the first array of spots to dry for 48-72 hours.

12. The method of claim 1, further comprising allowing the second array of spots to dry for 72-96 hours.

13. The method of claim 1, further comprising allowing the third array of spots to dry for 3-5 days.

14. The method of claim 1, further comprising including a fluorescent dye in one of the arrays of spots, and imaging the spots using a fluorescent imaging device.

15. The method of claim 2, wherein the nucleic acid solution includes an RNA and an expression vector.

16. The method of claim 15, wherein the RNA in the nucleic acid solution includes an siRNA, a μRNA, or a non-coding RNA.

17. The method of claim 15, wherein the expression vector in the nucleic acid solution includes a cDNA expression, or an shRNA expression.

18. The method of claim 2, wherein the nucleic acid solution includes a fluorescent dye labelled nucleotide and an siRNA directed toward NFkB subunit p65.

19. The method of claim 1, further comprising storing one of the printed arrays before overlay printing of another array.

20. The method of claim 1, further comprising printing one of the arrays of spots using 330 μm outer diameter capillary tubes.

21. The method of claim 1, further comprising printing one of the arrays of spots using 400 μm outer diameter capillary tubes.

22. The method of claim 1, wherein at least one printed array of spots includes spots of a different size to spots included in another array of printed spots.

23. The method of claim 4, wherein the concentration of gelatin in the gelatin solution is in the range 0.4% to 3.2% w/v.

24. The method of claim 1, wherein the first, second and third arrays of spots substantially coincide and form layered transfection arrays on the substrate when dry.

25. The method of claim 1, wherein the layered arrays of spots of reagent compositions are each printed by:
    displacing an array of reagent composition containing capillary tubes arranged alongside one another and each having at least one open end, with the open ends of the tubes being aligned, from an inoperative position to an operative position in which the open ends of the capillary tubes simultaneously impinge against a substrate, so that at least some reagent composition from the capillary tubes is thereby deposited on the substrate as spots, thereby to form an array of spots of the reagent compositions on the substrate; and
    thereafter displacing the array of capillary tubes from the operative position back to the inoperative position.

26. The method of claim 25, further including, after the array of capillary tubes has been displaced back to its inoperative position, or while it is being so displaced, replacing the substrate bearing the array of spots with another substrate, and repeating the displacement of the array of capillary tubes from its inoperative position to its operative position, and back to its inoperative position.

27. The method of claim 26, further including, before the displacing of the array of capillary tubes from the inoperative position to the operative position, forming the array of capillary tubes by supporting the capillary tubes on or against a plurality of supporting elements, with each supporting element supporting a plurality of the tubes and stacking the supporting elements into a print head assembly, with the displacing of the capillary tubes being effected by moving the print head assembly.

* * * * *